(12) United States Patent
Utsunomiya (10) Patent No.: US 8,992,016 B2
(45) Date of Patent: Mar. 31, 2015

(54) IMAGE SENSING APPARATUS USING OPTICAL COHERENCE TOMOGRAPHY AND CONTROL METHOD THEREFOR

(71) Applicant: Canon Kabushiki Kaisha, Tokyo (JP)

(72) Inventor: Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/898,538

(22) Filed: May 21, 2013

(65) Prior Publication Data

US 2013/0250238 A1 Sep. 26, 2013

Related U.S. Application Data

(62) Division of application No. 12/841,544, filed on Jul. 22, 2010, now Pat. No. 8,469,514.

(30) Foreign Application Priority Data

Aug. 4, 2009 (JP) .................................. 2009-181607

(51) Int. Cl.
*A61B 3/14* (2006.01)
*A61B 3/00* (2006.01)
*A61B 3/10* (2006.01)
*G01B 9/02* (2006.01)

(52) U.S. Cl.
CPC ............... *A61B 3/102* (2013.01); *A61B 3/0058* (2013.01); *G01B 9/02027* (2013.01); *G01B 9/02089* (2013.01); *G01B 9/02091* (2013.01); *G01B 2290/45* (2013.01)
USPC .......................................... 351/206; 351/246

(58) Field of Classification Search
USPC .................................................. 351/200–246
See application file for complete search history.

(56) References Cited

U.S. PATENT DOCUMENTS

| | | | |
|---|---|---|---|
| 7,229,175 B2 * | 6/2007 | Itoh | 351/206 |
| 7,272,304 B2 * | 9/2007 | Fukui | 396/48 |
| 7,347,553 B2 * | 3/2008 | Matsumoto | 351/214 |
| 7,438,413 B2 * | 10/2008 | Kashiwagi et al. | 351/206 |
| 7,445,337 B2 | 11/2008 | Sekiguchi | |
| 7,510,282 B2 | 3/2009 | Ueno et al. | |
| 7,566,128 B2 | 7/2009 | Tsukada et al. | |
| 7,639,845 B2 | 12/2009 | Utsunomiya | |
| 7,784,942 B2 | 8/2010 | Maeda et al. | |
| 7,995,132 B2 * | 8/2011 | Miyata et al. | 348/362 |

(Continued)

FOREIGN PATENT DOCUMENTS

| JP | 2007-117714 A | 5/2007 |
|---|---|---|
| JP | 2008-029467 A | 2/2008 |

(Continued)

*Primary Examiner* — Mohammed Hasan
(74) *Attorney, Agent, or Firm* — Fitzpatrick, Cella, Harper & Scinto (57) ABSTRACT

Tomographic images of a plurality of planes at a disease site of a fundus are taken exactly within a short period of time, and the tomographic images are respectively displayed so that the positional relationship thereof becomes clear. A low coherent optical tomographic image sensing apparatus for imaging a fundus includes a sensing unit which takes tomographic images of a plurality of planes intersecting each other in time division, a display unit which displays the taken tomographic images at separate sites on the identical screen, and a position indication unit which displays, in each tomographic image, an intersection position of the tomographic image and another tomographic image intersecting one another.

29 Claims, 6 Drawing Sheets

(56) References Cited

U.S. PATENT DOCUMENTS

| | | |
|---|---|---|
| 8,204,300 B2 | 6/2012 | Sugita et al. |
| 8,384,908 B2 | 2/2013 | Sugita et al. |
| 8,425,036 B2 | 4/2013 | Yoshida et al. |
| 8,469,514 B2 * | 6/2013 | Utsunomiya ............ 351/206 |
| 2007/0070295 A1 | 3/2007 | Tsukada et al. |
| 2008/0024721 A1 | 1/2008 | Ueno et al. |
| 2008/0084538 A1 | 4/2008 | Maeda et al. |
| 2009/0149742 A1 * | 6/2009 | Kato et al. ............ 600/425 |
| 2010/0166293 A1 | 7/2010 | Sugita et al. |
| 2010/0182610 A1 | 7/2010 | Utsunomiya |
| 2010/0182612 A1 | 7/2010 | Yoshida et al. |
| 2011/0032479 A1 | 2/2011 | Utsunomiya |
| 2011/0176107 A1 | 7/2011 | Yoshida et al. |
| 2012/0218557 A1 | 8/2012 | Sugita et al. |
| 2013/0250238 A1 | 9/2013 | Utsunomiya |

FOREIGN PATENT DOCUMENTS

| | | |
|---|---|---|
| JP | 2008-086670 A | 4/2008 |
| JP | 2008-298767 A1 | 12/2008 |
| JP | 2009-142313 A | 7/2009 |
| JP | 2009-160190 A | 7/2009 |
| JP | 2011-030887 A | 2/2011 |
| JP | 5426960 B2 | 2/2014 |

\* cited by examiner

IMAGE SENSING APPARATUS USING OPTICAL COHERENCE TOMOGRAPHY AND CONTROL METHOD THEREFOR

The application is a division of application Ser. No. 12/841,544 filed Jul. 22, 2010 Now U.S. Pat. No. 8,469,541 B2.

BACKGROUND OF THE INVENTION

1. Field of the Invention

The present invention relates to an image sensing apparatus using optical coherence tomography utilized in ophthalmic care, and the like, and also to a method of controlling the image sensing apparatus.

2. Description of the Related Art

Currently, various pieces of optical equipment have been used as ophthalmic equipment. Of those, as optical equipment observing eyes, various pieces of equipment such as an anterior segment photographing machine, a fundus camera, a scanning laser ophthalmoscope (SLO), and an image sensing apparatus (hereinafter, referred to as "OCT apparatus") using optical coherence tomography (OCT) have been used. Of those, the OCT apparatus takes a tomographic image of a fundus with high resolution.

The OCT apparatus irradiates a sample typified by a retina with low coherent light and measures reflected light from the sample with high sensitivity, using an interferometer. Further, the OCT apparatus scans the sample with the low coherent light and allows the reflected return light and reference light from the same light source, which has passed through a reference optical path, to interfere with each other, to thereby take a tomographic image. Such an OCT apparatus has been widely used in ophthalmic diagnosis particularly for taking a tomographic image of a retina.

The OCT apparatus takes a tomogram, and hence, may only take an image of one cross-section at a certain timing with a single interferometer configuration. Therefore, it is difficult to take a tomographic image in a cross-section passing through a disease site exactly. In order to solve this problem, according to the technology disclosed by Japanese Patent Application Laid-Open No. 2008-029467, an example is illustrated in which an OCT tomographic image (B-scan image) and an SLO image are on displayed on the same screen, and in which an appropriate B-scan tomographic position is shown. However, there still remain problems that an image showing a disease is not always shown on the SLO image, and that needs for taking tomograms of a disease site with a plurality of OCT tomographic images may not be satisfied.

SUMMARY OF THE INVENTION

As described in the related background art, when an eye with disease is photographed using an OCT apparatus, it is necessary to take a tomographic image of a disease site exactly. Further, it is desired that, in addition to a tomographic image of a plane parallel to an eye axis (so-called B-scan image), an image of a plane perpendicular to the eye axis (so-called C-scan image) be taken. It is an object of the present invention to take tomographic images of a plurality of different planes at a disease site of a fundus exactly, and display the tomographic images so that the positional relationship thereof becomes clear.

An image sensing apparatus using optical coherence tomography according to the present invention includes: a sensing unit which takes tomographic images of a plurality of planes intersecting each other in time division; a display unit which displays the tomographic images of the plurality of planes; and a position indication unit which displays intersection positions of the plurality of planes intersecting each other on each displayed tomographic image or in a vicinity of the each displayed tomographic image.

Further, an image sensing apparatus using optical coherence tomography according to the present invention includes: a first unit which displays a first tomographic image of a subject's eye in a first area of a display screen; a second unit which displays a second tomographic image of a plane intersecting a plane along which the first tomographic image is taken in a second area of the display screen; a position indication unit which displays information indicating a position where the plane along which the first tomographic image is taken and the plane along which the second tomographic image is taken intersect each other in each of the first area and the second area; a position change instruction unit which performs an operation of issuing a change instruction to change the position indicated by the information displayed in the first area; a sensing unit which changes the plane along which the second tomographic image to be displayed in the second area is taken to take a new second tomographic image based on the change instruction to change the position; and a position information change unit which changes information indicating a position where the plane along which the new second tomographic image is taken and the plane along which the first tomographic image is taken intersect each other.

Still further, a control method for an image sensing apparatus using optical coherence tomography according to the present invention includes: taking tomographic images of a plurality of planes intersecting each other in time division; displaying the tomographic images on the plurality of planes on an image display unit; and displaying intersection positions of the plurality of planes intersecting each other on each displayed tomographic image or in a vicinity of the each displayed tomographic image.

Further, an image sensing apparatus according to the present invention takes an optical coherence tomographic image of a subject's eye, using combined light obtained by combining return light from the subject's eye irradiated with sensing light with reference light corresponding to the sensing light, and includes: an instruction unit which performs an operation of issuing an instruction on a plurality of planes intersecting each other, using the optical coherence tomographic image of the subject's eye; and a sensing unit which takes the optical coherence tomographic image at a position based on the instruction from the instruction unit within a predetermined period of time.

According to the present invention, by displaying a tomographic position in a plane, the relationship in intersection position between planes at a time of taking respective tomographic images may be shown correctly.

Further features of the present invention will become apparent from the following description of exemplary embodiments with reference to the attached drawings.

DESCRIPTION OF THE EMBODIMENTS

An exemplary embodiment for carrying out the present invention is described with reference to the drawings.

<Display Portion of Image Sensing Apparatus Using Optical Coherence Tomography>

Figure 1:
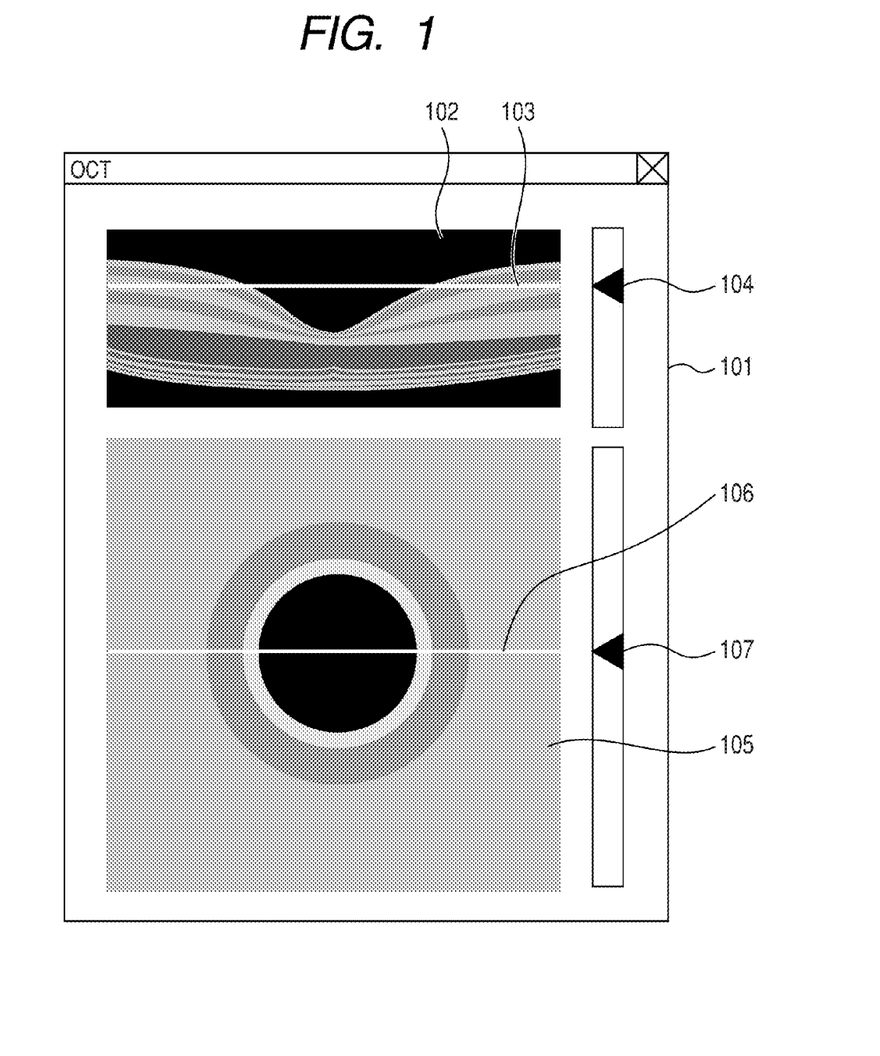
FIG. 1 is a screen display according to Example 1 of the present invention.

A display portion of an image sensing apparatus using optical coherence tomography for imaging a fundus according to this embodiment is described with reference to FIG. 1. On a display screen 101 of the image sensing apparatus, two cross-sections may be displayed. In FIG. 1, a tomographic image along a cross-section parallel to an eye axis, which is so-called a B-scan image 102, and a tomographic image along a cross-section orthogonal to the eye axis, which is so-called a C-scan image 105, are displayed. Thus, two taken tomographic images (first and second tomographic images) may be displayed in two areas (first and second areas) on the same screen. For example, a position on the B-scan image 102, where the cross-section along which the B-scan image 102 is taken and the cross-section along which the C-scan image 105 is taken intersect each other, is displayed as an intersection position 103. Similarly, a position on the C-scan image 105, where the cross-section along which the C-scan image 105 is taken and the cross-section along which the B-scan image 102 is taken intersect each other, is displayed as an intersection position 106. In order to perform an operation of issuing a change instruction to change the intersection position 103 on the display image, in other words, in order to perform an operation of issuing a change instruction to change a tomogram taking position of the C-scan image 105, a position change controller 104 (position change instruction unit) is provided. In order to change the intersection position 106 on the display image, in other words, in order to change a tomogram taking position of the B-scan image 102, a position change controller 107 (position change instruction unit) is provided.

Here, although the display screen 101 is illustrated in the form of a so-called graphic user interface (GUI), the display screen 101 is not limited thereto. Further, although a position indication unit indicating the intersection positions 103 and 106 is displayed using lines on the image in FIG. 1, the position indication unit may be displayed on the side of the image by an arrow or the like. Even in the case where the position indication unit is displayed using a line similarly as illustrated in FIG. 1, the line may be displayed in a flashing manner, so that the information on the image may be displayed to the examiner sufficiently. Further, the position change controllers 104 and 107 may be displayed in the form such as a slider based on the graphical user interface (GUI) as illustrated in FIG. 1. Alternatively, the position change controllers 104 and 107 may not be specifically displayed and the position changing operation may be conducted by an operation of a mouse wheel or a cursor of a keyboard after selecting an image. Further, although FIG. 1 illustrates a display image with two cross-sections, three or more cross-sections may be displayed on the same screen.

<Image Sensing Apparatus Using Optical Coherence Tomography>

Figure 2A:
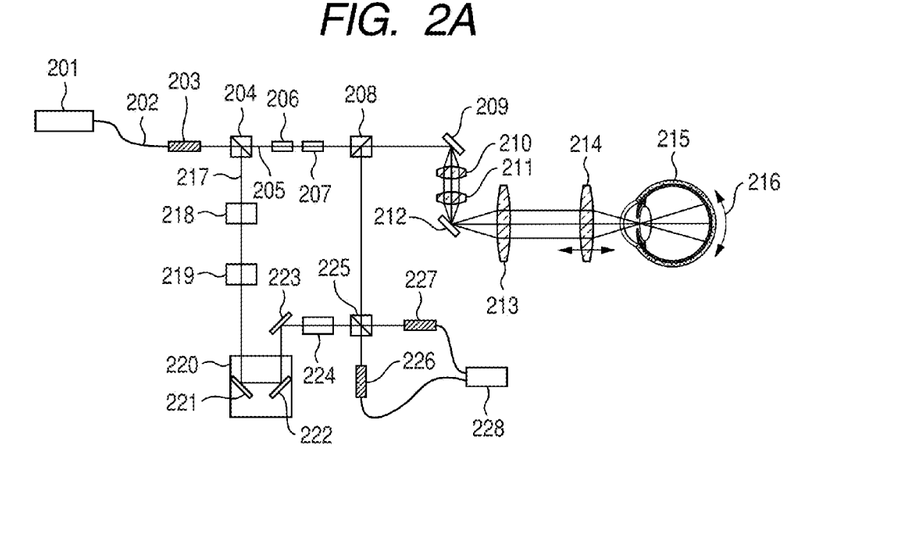
FIG. 2A is a schematic view of an apparatus according to Example 1 of the present invention.

An image sensing apparatus using optical coherence tomography for imaging a fundus, according to this embodiment, is described with reference to FIG. 2A. As a low coherent light source 201, a super luminescent diode (SLD) light source or an amplified spontaneous emission (ASE) light source may be used.

The wavelength of light to be used may be in a wavelength region in the vicinity of 850 nm or 1,050 nm suited for fundus diagnosis.

A swept source (SS) may also be used. In this case, however, the apparatus naturally needs to employ a swept-source optical coherence tomograph (SS-OCT) system, unlike the configuration of FIG. 2A. Light emitted from a light source 201 is guided to a fiber collimator 203 via an optical fiber 202, and the fiber collimator 203 functions to guide the light from the light source 201 to an interferometer as collimated light. A beam splitter 204 splits the collimated light into reference light and sample light. Along an optical path 205 of the sample light, dispersion-compensating glasses 206 and 207, a beam splitter 208, a galvanoscanner 209 for x-axis (horizontal) scanning, lenses 210 and 211, and a galvanoscanner 212 for Y-axis (vertical) scanning, complying with acousto-optical modulators (AOMs) to be described later, are disposed in the stated order. The sample light reaches the fundus of a subject's eye 215 through lenses 213 and 214 and is allowed to scan the fundus by the galvanoscanners 209 and 212 in directions indicated by an arrow 216. Here, the lens 214 also serves as a focusing lens, and hence the lens 214 is capable of moving in directions indicated by an arrow of FIG. 2A and changing a focal position of an image sensing system according to the refraction state (myopia, hyperopia) of the subject's eye 215. The focal position of the image sensing system may be changed at a time of performing an operation of issuing a change instruction to change the intersection position of the scan image.

The reference light passes through acousto-optical modulators (AOMs) 218 and 219 disposed on an optical path 217. The AOMs 218 and 219 modulate the reference light with different frequencies, and as a result, the reference light is used under a condition of being modulated with a frequency difference. In the optical path 217 of the reference light, a stage 220 for making an optical path length of the reference light variable is disposed, and the optical path length of the reference light is made variable by mirrors 221 and 222 on the stage 220. Here, as the stage 220, a linear motor stage, a voice coil motor stage, or an ultrasonic motor stage may be used. The reference light further passes through a mirror 223 and a dispersion-compensating glass 224 placed in the optical path 217, and reaches a beam splitter 225 for combining the reference light with the sample light. The dispersion-compensating glass 224 is for removing influences exerted by the lenses and the like disposed in the optical path 205 of the sample light and moisture in the eyeball.

The sample light and the reference light obtained by the fiber collimators 226 and 227 are guided via fibers, respectively, to a processing portion 228 including a balanced detector described later, and are subjected to the detection and imaging of an interference signal, the display of an image, and the like.

The configuration of the interferometer is described above. The above-mentioned embodiment includes a time-domain OCT apparatus capable of performing transverse scanning (in-plane scanning). More specifically, an apparatus configuration according to this embodiment is capable of taking a B-scan image and a C-scan image in time division. The transverse scanning OCT apparatus described in the present invention refers to a time-domain OCT apparatus which has a main scanning direction perpendicular to an eye axis. A low coherent tomographic image sensing apparatus according to the present invention only needs to take tomographic images of different cross-sections intersecting each other in time division, and is not necessarily limited to a time-domain OCT apparatus capable of performing transverse scanning. More specifically, as well as a spectral domain OCT (SD-OCT) apparatus and a swept source OCT (SS-OCT) apparatus that is a Fourier-domain OCT apparatus, a transverse scanning OCT (TS-OCT) apparatus that is a time-domain OCT apparatus may also be used. An OCT apparatus capable of switching each apparatus in time division may be used. Needless to say, this embodiment may include a Mach-Zehnder interferometer or a Michelson interferometer.

EXAMPLES

Example 1

An image sensing apparatus using optical coherence tomography according to Example 1 is as follows.
<Display Screen>
First, a display portion of the image sensing apparatus is described in detail with reference to FIG. 1. On a display screen 101 of the image sensing apparatus, tomographic images (first and second tomographic images) along two cross-sections may be displayed in two respective corresponding areas (first and second areas). A first tomographic image along a cross-section parallel to an eye axis, which is so-called a B-scan image 102, and a second tomographic image along a cross-section orthogonal to the eye axis, which is so-called a C-scan image 105, are displayed. An intersection position 103 on the B-scan image 102, where the cross-section along which the B-scan image 102 is taken and the cross-section along which the C-scan image 105 is taken intersect each other, is indicated using a line by a position indication unit. Similarly, an intersection position 106 on the C-scan image, where the cross-section along which the C-scan image 105 is taken and the cross-section along which the scan image 102 is taken intersect each other, is indicated by a line. In order to change the intersection position 103, in other words, in order to change the position where the tomographic image of the C-scan image 105 is taken, a first position change controller 104 (first position change instruction unit) is provided. In order to change the intersection position 106, in other words, in order to change the position where the tomographic image of the B-scan image 102 is taken, the second position change controller 107 (second position change instruction unit) is provided.
<Apparatus Configuration>
Next, the image sensing apparatus for imaging a fundus according to Example 1 is described with reference to FIG. 2A. As a low coherent light source 201, a super luminescent diode (SLD) light source having a center wavelength of 840 nm is used. Light emitted from the light source is guided to an interferometer as collimated light via a single-mode optical fiber 202 by a fiber collimator 203.

Then, the collimated light is split into reference light and sample light by a beam splitter 204. The sample light reaches a beam splitter 208 through dispersion-compensating glasses 206 and 207, complying with acousto-optical modulators (AOMs) to be described later, which are disposed in the optical path 205. The sample light further passes through a galvanoscanner 209 for X-axis (horizontal) scanning, lenses 210 and 211, a galvanoscanner 212 for Y-axis (vertical) scanning, and lenses 213 and 214, to thereby reach a fundus of a subject's eye 215. The galvanoscanners 209 and 212 allow reference light to scan the fundus in directions indicated by an arrow 216. Here, the lens 214 also serves as a focusing lens, and hence is capable of moving in directions indicated by an arrow with a stage (not shown). The focal position of the image sensing system may be changed according to the refraction state (myopia, hyperopia) of the subject's eye 215. The reference light passes through acousto-optical modulators (AOMs) 218 and 219 disposed on an optical path 217. The AOMs 218 and 219 modulate the reference light with 40 MHz and 41 MHz, and as a result, the reference light is used under a condition of being modulated with 1 MHz. On a stage 220 for making the optical path length of the reference light variable, mirrors 221 and 222 are mounted. Here, as the stage 220, a linear motor stage is used. The reference light further passes through a mirror 223 and a dispersion-compensating glass 224 provided for the purpose of removing influences exerted by the lenses and the like disposed in the optical path 205 of the sample light and moisture in the eyeball, and reaches a beam splitter 225 for combining the reference light with the sample light. The respective sample light and the reference light obtained by the fiber collimators 226 and 227 are guided to a processing portion 228 including a balanced detector to be described later via fibers, and subjected to the detection and imaging of an interference signal, the display of an image, and the like in the processing portion 228.
<Control Block Diagram and Control Waveform>
Next, the processing portion 228 of Example 2 is described with reference to the block diagram illustrated in FIG. 2B. The processing portion 228 includes a central processing unit 301 for performing entire control, a display screen 302 for displaying a tomographic image, a fixed disk device 30 for storing a control program and saving results, a main storage region 304 for reading the control program and processing acquired data, an operation interface 305 such as a keyboard or a mouse for operation by the examiner, a digital-to-analog (DA) converter 306 for generating a waveform for controlling an actuator to be described later, a scanner driver 307 for driving an X-axis scanner, a scanner driver 308 for driving a Y-axis scanner, a stage controller 309 for driving a stage for changing an optical path length of reference light, and a stage controller 310 for driving a lens for driving a lens for focusing. The drivers 307 and 308 and the controllers 309 and 310 form an analog servo mechanism following the control waveform generated by the DA converter 306. The waveform for controlling the drivers 307 and 308 and the controllers 309 and 310 is described later. A balanced detector 313 for receiving an interference signal and converting the signal into a voltage takes out an interference signal with a frequency in the vicinity of 1 MHz (herein, in a frequency band of 500 kHz to 1.5 MHz) by a bandpass filter 312, converts the interference signal into a digital value by an analog-to-digital (AD) converter 311, and images the digital value. The taking of one image is synchronized with a frame taking trigger waveform signal 314. The frame taking trigger waveform signal 314 is generated by the DA converter 306 in the form of being synchronized with a control waveform of each actuator.

Figure 2B:
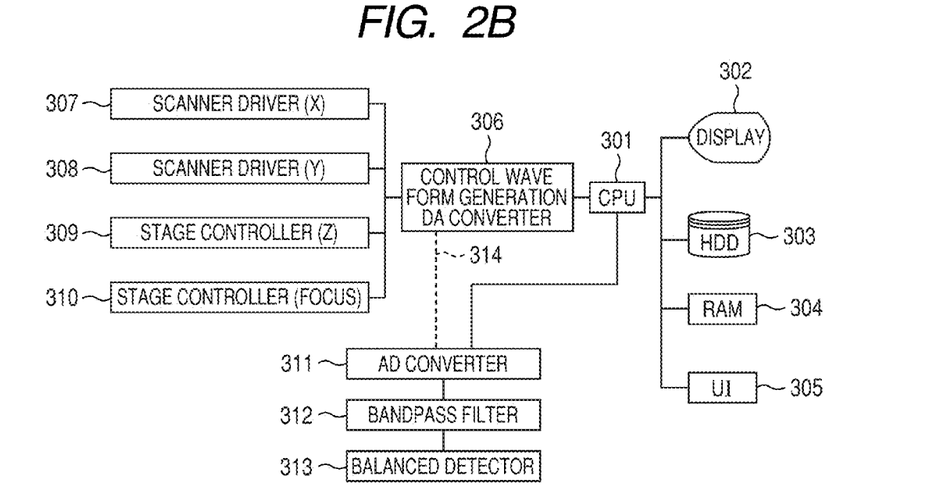
FIG. 2B is a control block diagram in the apparatus.

The AD converter 311 is operated based on a rising signal of the frame taking trigger waveform signal 314 and acquires data with a data length of one frame. The amplitude of the data is obtained and imaged, to thereby generate a tomographic image.

Figure 3:
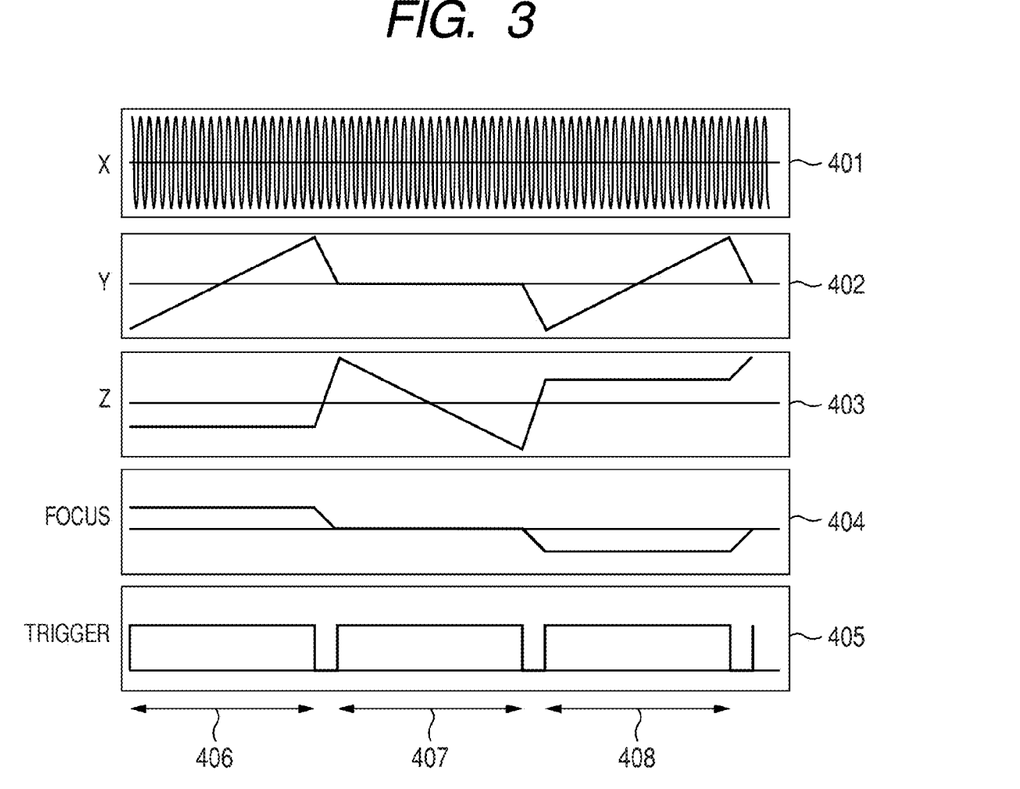
FIG. 3 is a control waveform diagram according to Example 1 of the present invention.

Next, a control waveform signal and an actual control operation are described with reference to FIGS. 1 and 3.

A control waveform signal 401 of the X-axis galvanoscanner 209 is a signal for scanning with a sine wave of 500 Hz. A control waveform signal 402 of the Y-axis galvanoscanner 212, a stage control waveform signal 403 for adjusting an optical wavelength of reference light, and a stage control waveform signal 404 for focusing are signals for driving the respective corresponding actuators. These signals are generated periodically.

The respective control waveform signals 402, 403, and 404 drive the actuators as described later. The waveform signal 405 is a frame taking trigger waveform signal. At each rising time, signal recording is started, and at each falling time, signal recording is ended. Periods 406, 407, and 408 respectively indicate time it takes to take data on one frame (tomographic image). During the period 406, the Y-axis is scanned at an equal speed with the Z-axis fixed, and a C-scan image may be taken. At this time, the Z-axis that is an optical path length of reference light is fixed at a position corresponding to the position 103 illustrated in FIG. 1. Similarly, a focus is also fixed at a focus position (where a Z-position of the fundus is focused) corresponding to the Z-position 103. The tomographic image taken during the period 406 is displayed in the area 105 of FIG. 1 (display is updated). During the period 407, the Z-axis is scanned with the Y-axis 402 fixed, and hence a B-scan image may be taken. At this time, the stage control waveform signal 404 for focusing is fixed at an intermediate position in a Z-direction.

Here, the focus position may be scanned according to the Z-position. A tomographic image taken during the period 407 is displayed in the first area of FIG. 1 (display is updated). Here, if the position change controller 104 of FIG. 1 is operated, a tomographic position of the C-scan image needs to be changed after the operation of issuing a change instruction of an intersection position is performed. At a time of generating a waveform during the period 408, the waveform signal 403 on the Z-axis and the waveform signal 404 on the focus axis are changed to the respective corresponding positions. Further, in synchronization with the generation of a waveform during the period 408, the illustrated pattern at the intersection position 103 of FIG. 1 is moved to a corresponding depth (position). Similarly, even in the case where the position change controller 107 is operated, the fixed position on the Y-axis of a subsequent B-scan taking timing corresponding to the period 407 is changed. In this manner, a tomographic image is taken at a changed position based on the position change instruction, and the positional information indicating the position where tomographic images intersect each other is changed.

With the above-mentioned control function, the examiner is capable of recording tomograms along two cross-sections at appropriate positions during photographing the subject.

Example 2

An image sensing apparatus using optical coherence tomography according to Example 2 is as follows.

<Display Screen>

Figure 4:
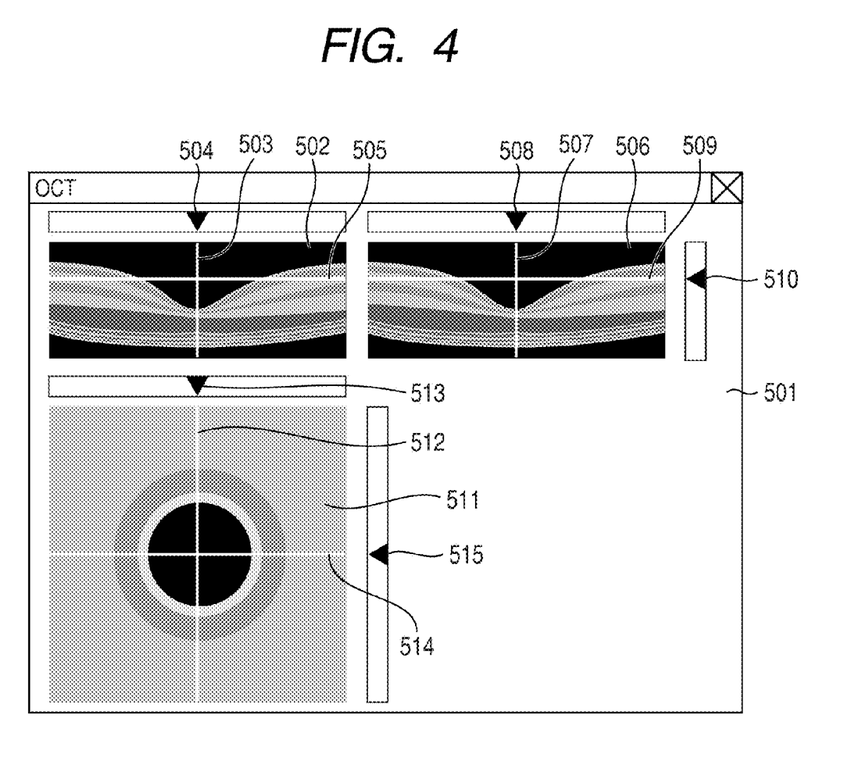
FIG. 4 is a screen display according to Example 2 of the present invention.

First, a display portion of the image sensing apparatus using optical coherence tomography according to Example 2 is described with reference to FIG. 4. On a display screen 501 of the image sensing apparatus, tomographic images (first, second, and third tomographic images) along three cross-sections may be displayed in three respective corresponding areas (first, second, and third areas). On the display screen 501, tomographic images along a cross-section parallel to an eye axis which are so-called B-scan images 502 and 506, and a tomographic image along a cross-section orthogonal to the eye axis, which is so-called C-scan image 511, are displayed. In the B-scan images 502 and 506, intersection positions 514 and 512 are displayed, respectively, as positions corresponding to cross-sections along which a tomographic image of the C-scan image 511 is taken.

More specifically, the B-scan image 502 is a cross-sectional image (cross-sectional image of a horizontal plane when a subject stands upright), and the B-scan image 506 is a cross-sectional image (cross-sectional image of a vertical plane when the subject stands upright) in the Y-axis direction. The intersection position 503 indicates a cross-sectional intersection site of the B-scan image 502 with respect to the B-scan image 506. A controller (position change instruction unit) 504 serves to change the position of the intersection position 503 with respect to the B-scan image 506. The intersection position 505 indicates a cross-sectional intersection site in the B-scan image 502 with respect to the C-scan image 511. The intersection position 507 indicates a cross-sectional intersection site in the B-scan image 506 with respect to the B-scan image 502. The intersection position 509 indicates, similarly to the intersection position 505, a cross-sectional intersection site of the B-scan image 506 with respect to the C-scan image 511. A controller 508 serves to change the position of the intersection position 502 in the B-scan image 506, and a controller 510 serves to change the intersection position 509 of the C-scan image 511 in the B-scan image 506. The intersection position 512 indicates a cross-sectional intersection site of the B-scan image 506 in the C-scan image 511, and the intersection position 514 indicates a cross-sectional intersection site of the B-scan image 502 in the C-scan image 511. A controller 513 is operated in association with the controller 504, and serves to change the position of the B-scan image 506 in the C-scan image 511. A controller 515 serves to change the position of the B-scan image 502 in the C-scan image 511. The intersection positions are all indicated by lines as the position display units.

<Apparatus Configuration>

Figure 5A:
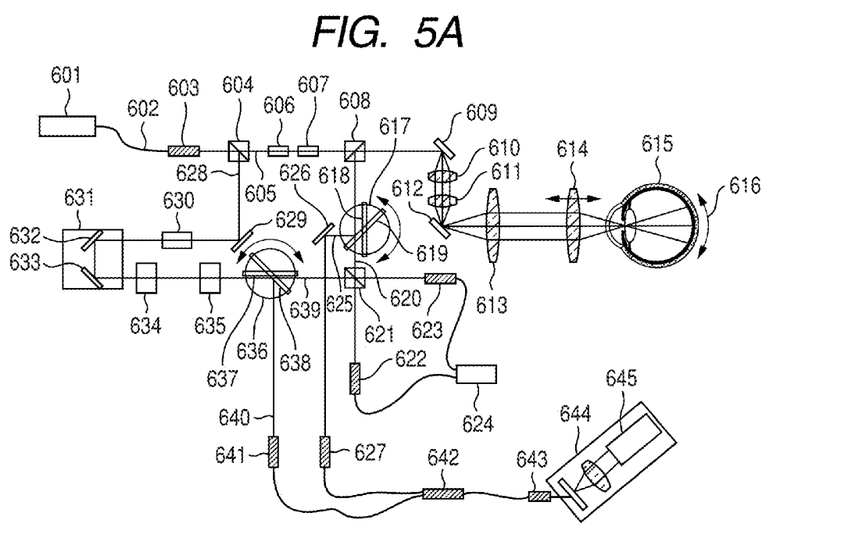
FIG. 5A is a schematic view of an apparatus according to Example 2 of the present invention.

An apparatus configuration of the image sensing apparatus according to Example 2 is described with reference to FIG. 5A. Example 2 is illustrated as a configuration example in which a transverse OCT apparatus (TS-OCT apparatus) is combined with a spectral domain OCT apparatus (SD-OCT apparatus). As a low coherent light source 601, a super luminescent diode (SLD) that emits light having a center wavelength of 840 nm is used. The light emitted from the light source 601 is guided to a fiber collimator 603 via a single mode optical fiber 602, and is further guided to an interferometer through the fiber collimator 603 as collimated light. The collimated light is split into reference light and sample light by a beam splitter 604. The sample light guided to an optical path 605 reaches a beam splitter 608 through dispersion-compensating glasses 606 and 607, complying with acousto-optical modulators (AOMS) to be described later. The sample light further passes through a galvanoscanner 609 for X-axis (horizontal) scanning, lenses 610 and 611, and a galvanoscanner 612 for Y-axis (vertical) scanning, and reaches a fundus plane of a subject's eye 615 through lenses 613 and 614. The sample light is allowed to scan the fundus plane by the galvanoscanners 609 and 612 in directions indicated by an arrow 616. Here, the lens 614 also serves as a focusing lens, and hence is capable of being moved by a stage (not shown) in directions indicated by an arrow illustrated in the drawing. The lens 614 may change a focal position of the image sensing system according to the refraction state (myopia, hyperopia) of a subject's eye 615. The sample light reflected by the fundus plane of the subject's eye 615 passes through the lenses, the scanners, and the like described above again in a reverse direction, and is guided to an optical path switching device 617 by the beam splitter 608. According to Example 2, when the optical path switching device 617 is in a state 618, the sample light is guided to an optical path 620 directed to the TS-OCT apparatus, and when the optical path switching device 617 is in a state 619, the sample light is guided to an optical path 625 directed to the SD-OCT apparatus. Therefore, a mirror is rotated in the optical path switching device 617, and an actuator of a solenoid is used for the rotation. When the TS-OCT apparatus is used, the sample light is guided to a beam splitter 621 so that the sample light is combined with the reference light. The sample light and the reference light collected respectively by the fiber collimators 622 and 623 are guided to a processing portion 624 to be described later via a fiber. Based on the lights, a TS-OCT signal is acquired by a balanced detector included in the processing portion 624. In the optical path 625 when the SD-OCT apparatus is used, the sample light is guided to a mirror 626, and is further guided to a fiber coupler 642 by a fiber collimator 627.

In an optical path 628, the reference light is guided to a mirror 629. The reference light further passes through lenses disposed in the optical path 605 of the sample light and a dispersion-compensating glass 630 corresponding to water (vitreous body, crystalline lens, aqueous humor) of the subject's eye, and reaches a stage 631 for changing an optical path length of the reference light. Here, a linear motor stage is used. The reference light is returned by mirrors 632 and 633 provided on the stage 631, and guided to acousto-optical modulators (AOMs) 634 and 635. Here, when the TS-OCT apparatus is used, the reference light is modulated with 40 MHz and 41 MHz, and as a result, the reference light is used under a condition of being modulated with 1 MHz. When the SD-OCT apparatus is used, the reference light is put in a state of 40 MHz, and thus, the reference light is used without being modulated. An optical path switching device 636 serves as an optical path 639 when the TS-OCT apparatus is used in a state 637, and serves as an optical path 640 when the SD-OCT apparatus is used in a state 638. In the mechanism, a mirror is rotated using a solenoid in the same way as in the optical path switching device 617. When the optical path 639 at a time of the use of the TS-OCT apparatus is selected, the reference light is guided to the beam splitter 621. When the optical path 640 at a time of the use of the SD-OCT apparatus is selected, the reference light is guided to the fiber collimator 641. The sample light and the reference light at a time of the use of the SD-OCT apparatus, guided by the fiber collimators 627 and 641, are combined by the fiber coupler 642. After that, the combined light is output from the fiber collimator 643, dispersed by a spectroscope 644, received by a line sensor camera 645, and data thus obtained are sent to the processing portion 624.

<Control Block Diagram and Control Waveform>

Figure 5B:
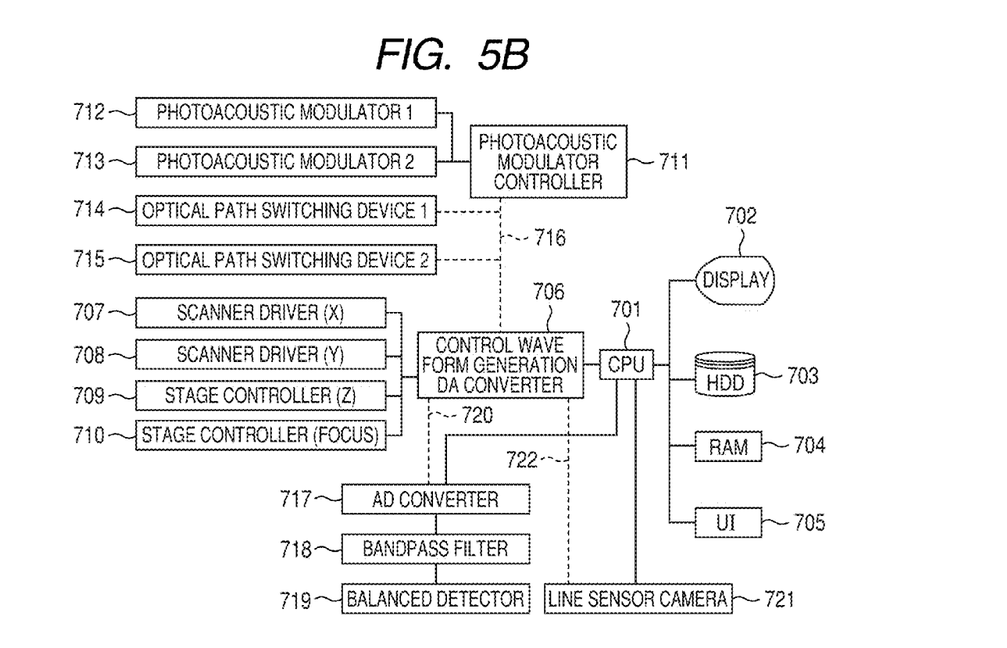
FIG. 5B is a control block diagram in the apparatus.

A block diagram of the processing portion 624 of the image sensing apparatus according to Example 2 is described with reference to FIG. 5B. The processing portion 624 includes a central processing unit 701 for performing entire control, a display screen 702 for displaying a tomographic image, a fixed disk device 703 for storing a control program and saving results, a main storage region 704 for reading the control program and processing acquired data, an operation interface 705 such as a keyboard or a mouse for operation by the examiner, a DA converter 706 for generating a waveform for controlling an actuator to be described later, a scanner driver 707 for driving an X-axis scanner 609, a scanner driver 708 for driving a Y-axis scanner 612, a stage controller 709 for driving a stage 631 for changing an optical path length of reference light, and a stage controller 710 for driving a lens 614 for driving a lens for focusing. The scanner drivers 707 and 708 and the controllers 709 and 710 form an analog servo mechanism following the control waveform generated by the DA converter 706. The waveform controlling the scanner drivers 707 and 708 and the controllers 709 and 710 is described later. Further, a controller 711 of the acousto-optical modulator controls acousto-optical modulators 712 and 713. Here, the acousto-optical modulator 712 is always set to 40 MHz when using the TS-OCT system and the SD-OCT system, while the acousto-optical modulator 713 is switched between 41 MHz when using the TS-OCT system and 40 MHz when using the SD-OCT system. The switching is performed based on an OCT switching signal 716. The optical path switching devices 714 and 715 in FIG. 5B correspond to the optical path switching devices 617 and 636 of FIG. 5A, and switch an optical path based on the OCT switching signal 716.

A balanced detector 719 for receiving an interference signal and converting the signal into a voltage takes a signal, and the signal is taken out with a frequency in the vicinity of 1 MHz (herein, in a frequency band of 500 kHz to 1.5 MHz) by a bandpass filter 718. The signal thus taken out is converted into a digital value by an AD converter 717, and then the digital value is imaged. The taking of one image is synchronized with a TS-OCT system frame taking trigger waveform signal 720. The frame taking trigger waveform signal 720 is generated by the DA converter 706 in the form of being synchronized with a control waveform of each actuator.

Figure 6:
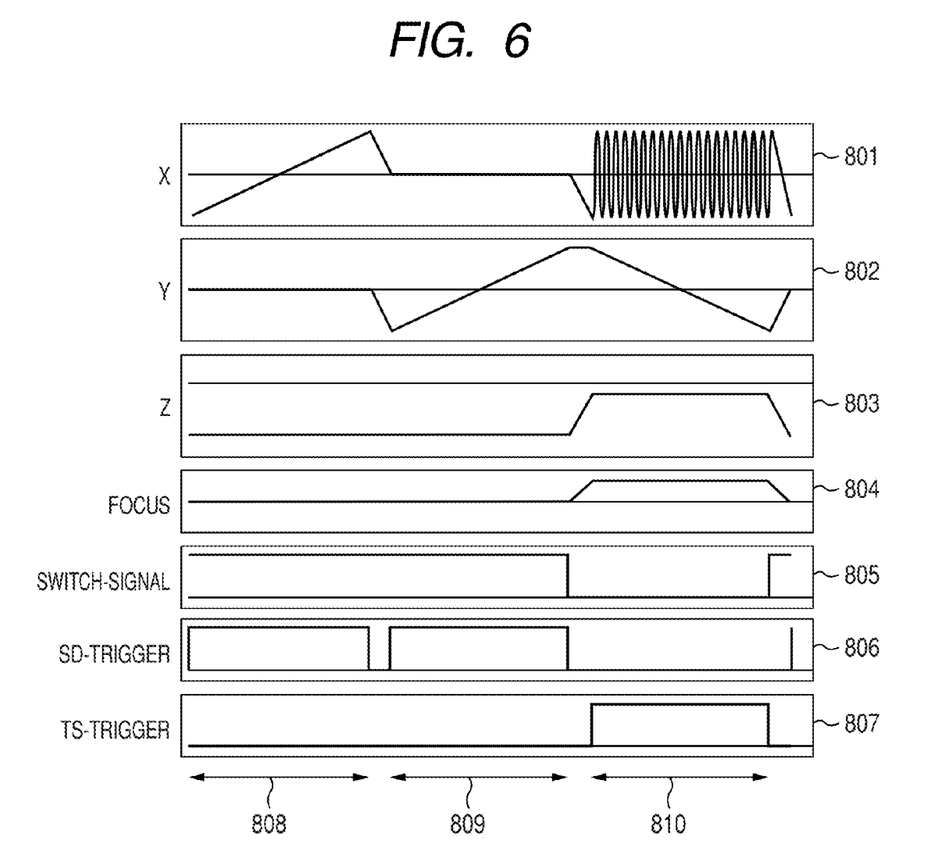
FIG. 6 is a control waveform diagram according to Example 2 of the present invention.

The AD converter 717 is operated based on a rising signal of the frame taking waveform trigger signal 720 and acquires data with a data length of one frame. The amplitude of the data is obtained and imaged, to thereby generate a tomographic image. Signals are fetched by the line sensor camera 721 of the spectroscope for the SD-OCT system based on the rising of a fetching signal 722 of the SD-OCT system. In the line sensor camera 721, a plurality of fetched spectral signals are subjected to Fourier transform, so that a tomographic image may be obtained. Next, the control waveform and an actual control operation are described with reference to FIGS. 4 to 6. FIG. 6 illustrates a control waveform signal 801 of the X-axis galvanoscanner, a control waveform signal 802 of the Y-axis galvanoscanner, a stage control waveform signal 803 for adjusting an optical path length of the reference light, and a stage control waveform signal 804 for focusing.

The respective control waveform signals 801 to 804 are driven as described later. An OCT switching signal 805 switches an interferometer to the use state of the SD-OCT apparatus when the signal is at a high level. More specifically, the OCT switching signal 805 sets the optical path switching device 617 of FIG. 5A at the state 619 and sets the optical path switching device 636 at the state 638, and the controller 711 of FIG. 5B switches the frequency of the acousto-optical modulator 713 to 40 MHz. It should be understood that, when the signal is at a low level, the interferometer is switched to the use state of the TS-OCT apparatus. More specifically, the optical path switching device 617 of FIG. 5A is set at the state 618, and the optical path switching device 636 is set at the state 637, and the controller 711 of FIG. 5B switches the frequency of the acousto-optical modulator 713 to 41 MHz. Here, although not related to the essence of the present invention, when the acousto-optical modulator 713 is switched, the angle of an optical path is changed slightly. This change is adjusted by the optical path switching device 636. A frame trigger waveform signal 806 of the SD-OCT system and a frame trigger control waveform signal 807 of the TS-OCT system cause an image to be taken. A taking time 808 in the SD-OCT system indicate a taking time of a B-scan tomographic image in the X-axis direction. The B-scan tomographic image is taken by the X-axis scanning based on the control waveform signal 801. A taking time of the B-scan tomographic image in the Y-axis direction is indicated by a taking time 809. The B-scan tomographic image is taken by the Y-axis scanning based on the control waveform signal 802. During the scanning conducted in the taking times 808 and 809, the Z-axis is driven to a position in front of the fundus (position corresponding to the vitreous body side) with the control waveform signal 803. Specifically, the Z-axis is driven to such a position that a mirror image is not formed while a signal is fetched in the SD-OCT system. The tomographic image taken during the taking time 808 is displayed in the area of FIG. 4 in which the B-scan image 502 is displayed. The tomographic image taken during the taking time 809 is displayed in the area of FIG. 4 in which the B-scan image 506 is displayed. The respective tomographic images are updated every time images are taken. During a taking time 810 in the TS-OCT system, an X-axis of the control waveform signal 801 is a signal for scanning with a sine wave of 500 Hz, a Y-axis of the control waveform signal 802 is a signal for scanning at an equal speed, and a Z-axis of the control waveform signal 803 is a signal to be fixed at a predetermined position. The fixed positions of the Z-axis by the control waveform signal 803 are positions corresponding to the intersection positions 505 and 509 of FIG. 4. Thus, a C-scan tomographic image is taken by the TS-OCT system during the taking time 810. It should be understood that, as in Example 1, regarding the control waveform signal 804 for focusing, it is desired to drive the Z-axis to a position corresponding to the position of the Z-axis of the control waveform signal 803. Further, when the respective controllers 504, 508, 510, 513, and 515 of FIG. 4 are operated, the controller 504 changes the position of the time 809 of the control waveform signal 801 (X), the controller 508 changes the position of the time 808 of the control waveform signal 802 (Y), the controller 510 changes the position of the time 810 of the control waveform signal 803 (Z), the controller 513 changes the position of the time 809 of the control waveform signal 801 (X), and the controller 515 changes the position of the time 808 of the control waveform signal 802 (Y) at a time of the generation of a next control waveform, and the controllers change the positions where cross-sections intersect each other on the screen similarly. The relationship between the controllers and the positions where the cross-sections intersect each other are as follows. The controller 504 corresponds to the intersection position 503 and the intersection position 512, the controller 508 corresponds to the intersection position 507 and the intersection position 514, the controller 510 corresponds to the intersection position 505 and the intersection position 509, the controller 513 corresponds to the intersection position 503 and the intersection position 512, and the controller 515 corresponds to the intersection position 507 and the intersection position 514, and the controllers may change the respective corresponding display positions. Thus, a tomographic image is taken at a changed position based on each position change instruction, and position information indicating the position where tomographic images intersect each other is changed.

With the above-mentioned control function, the examiner may exactly record tomographic images of three cross-sections at appropriate positions during photographing of a subject. This example illustrates a combination of the TS-OCT apparatus and the SD-OCT device. However, similar recording of images may be performed using the SD-OCT apparatus alone.

As described above, each example may show whether a plurality of tomographic images to be taken correspond to tomographic images of a disease site correctly to an examiner who is taking tomographic images of a fundus. Further, by displaying a position of a tomographic image in a plane, the relationship in intersection position between the tomographic images may be illustrated correctly. Further, in the case where a tomographic position change function is provided, when an image sensing position is shifted from a disease site, each intersection position may be changed to a correct tomographic position by a simple operation.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

As many apparently widely different embodiments of the present invention can be made without departing from the sprit and scope thereof, it is to be understood that the invention is not limited to the specific embodiment thereof except as defined in the appended claims.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-181607, filed Aug. 4, 2009, which is hereby incorporated by reference herein in its entirety.

What is claimed is:

1. An apparatus for taking tomographic images of an object using optical coherence tomography, the apparatus comprising:
    an instruction unit configured to instruct independently to change positions of a plurality of planes intersecting each other;
    a unit configured to take tomographic images of regions of the object corresponding to the positions in time division; and
    a display controlling unit configured to control a display unit to display the tomographic images and intersection positions of the plurality of planes intersecting each other on the displayed tomographic images or in a vicinity of the displayed tomographic images.

2. An apparatus according to claim 1, further comprising:
    a first position change operation unit which executes a position change of the intersection position on any one displayed tomographic image of the tomographic images of the plurality of planes; and
    an image replacing unit which changes the one displayed tomographic image to a tomographic image corresponding to the intersection position based on the position change.

3. An apparatus according to claim 2, further comprising a second position change operation unit which executes a position change of a focal position of an image sensing system at a time of the position change of the intersection position.

4. An apparatus according to claim 1, wherein the unit configured to take tomographic images employs a transverse scanning system.

5. An apparatus according to claim 1, wherein the unit configured to take tomographic images employs a Fourier-domain system.

6. An apparatus according to claim 1, wherein the unit configured to take tomographic images switches between a transverse scanning system and a Fourier domain system in time division.

7. An apparatus comprising:
a display controlling unit configured to control a display unit to display (a) a first tomographic image of an object in a first area of a display screen, (b) a second tomographic image of a plane intersecting a plane along the first tomographic image in a second area of the display screen, and (c) information indicating positions where the plane along the first tomographic image and the plane along the second tomographic image intersect each other in the first area and the second area;
an instruction unit configured to instruct independently to change the positions indicated by the information displayed in the first area and the second area; and
a unit configured to take a new second tomographic image of a plane corresponding to the changed position by using a scanning unit that scans the light on the object,
wherein the display controlling unit controls the display unit to display the new second tomographic image in the second area.

8. An apparatus according to claim 7, wherein the display controlling unit controls the display unit to display a third tomographic image of a plane intersecting the plane along the first tomographic image and the plane along the second tomographic image in a third area of the display screen,
wherein the display controlling unit is configured to control the display unit to display information indicating a position where the plane along the first tomographic image and the plane along the third tomographic image intersect each other in the first area and the third area,
wherein the instruction unit performs an operation of issuing a change instruction to change the position indicated by the information displayed in the third area, and
wherein the display controlling unit controls the display unit to display a new first tomographic image of a plane corresponding to the changed position in the first area.

9. An apparatus according to claim 7, wherein the object is a subject's eye, and
wherein the scanning unit is located so that the light scanned by the scanning unit passes through the same position on an anterior ocular segment of the subject's eye.

10. A control method for an apparatus for taking tomographic images of an object using optical coherence tomography, the control method comprising:
instructing independently to change positions of a plurality of planes intersecting each other;
taking tomographic images of regions of the object corresponding to the positions in time division; and
controlling a display unit to display the tomographic images and intersection positions of the plurality of planes intersecting each other on the displayed tomographic images or in a vicinity of the displayed tomographic images.

11. A non-transitory, computer-readable recording medium for storing a program causing a computer to execute the control method according to claim 10.

12. An apparatus for taking images of an object based on return light from the object irradiated with light, the apparatus comprising:

an instruction unit configured to instruct independently to change positions of a plurality of planes intersecting each other; and
a unit configured to take images of regions of the object corresponding to the changed positions by using a scanning unit that scans the light on the object.

13. An apparatus according to claim 12, wherein the object is a subject's eye, and
wherein the scanning unit is located so that the light scanned by the scanning unit passes through the same position on an anterior ocular segment of the subject's eye.

14. A method comprising:
displaying (a) a first tomographic image of an object in a first area of a display screen, (b) a second tomographic image of a plane intersecting a plane along the first tomographic image in a second area of the display screen, and (c) information indicating positions where the plane along the first tomographic image and the plane along the second tomographic image intersect each other in the first area and the second area;
instructing independently to change the positions indicated by the information displayed in the first area and the second area;
taking a new second tomographic image of a plane corresponding to the changed position by using a scanning unit that scans the light on the object; and
displaying the new second tomographic image in the second area.

15. A non-transitory, computer-readable recording medium for storing a program causing a computer to execute the method according to claim 14.

16. A method according to claim 14, wherein the object is a subject's eye, and
wherein the scanning unit is located so that the light scanned by the scanning unit passes through the same position on an anterior ocular segment of the subject's eye.

17. A method for taking images of an object based on return light from the object irradiated with light, the method comprising:
instructing independently to change positions of a plurality of planes intersecting each other; and
taking images of regions of the object corresponding to the changed positions by using a scanning unit that scans the light on the object.

18. A method according to claim 17, wherein the object is a subject's eye, and
wherein the scanning unit is located so that the light scanned by the scanning unit passes through the same position on an anterior ocular segment of the subject's eye.

19. A non-transitory tangible medium having recorded thereon a program for causing a computer to perform steps of the method according to claim 17.

20. An apparatus for taking images of an object based on return light from the object irradiated with light, the apparatus comprising:
an instruction unit configured to instruct independently to change positions of a plurality of planes intersecting each other; and
a unit configured to take images of regions of the object corresponding to the changed positions by controlling a scanning unit that scans the light on the object based on the instruction of the instruction unit.

21. An apparatus according to claim 20, wherein the object is a subject's eye, and wherein the scanning unit is located so that the light scanned by the scanning unit passes through the same position on an anterior ocular segment of the subject's eye.

22. A method for taking images of an object based on return light from the object irradiated with light, the method comprising:
instructing independently to change positions of a plurality of planes intersecting each other; and
taking images of regions of the object corresponding to the changed positions by controlling a scanning unit that scans the light on the object based on the instructing.

23. A non-transitory tangible medium having recorded thereon a program for causing a computer to perform steps of the method according to claim 22.

24. A method according to claim 22, wherein the object is a subject's eye, and
wherein the scanning unit is located so that the light scanned by the scanning unit passes through the same position on an anterior ocular segment of the subject's eye.

25. An apparatus for taking images of an object based on return light from the object irradiated with light, the apparatus comprising:
an instruction unit configured to instruct independently to change positions of a plurality of planes intersecting each other; and
a control unit configured to control a scanning unit to scan the light on regions of the object corresponding to the changed positions.

26. An apparatus according to claim 25, wherein the object is a subject's eye, and
wherein the scanning unit is located so that the light scanned by the scanning unit passes through the same position on an anterior ocular segment of the subject's eye.

27. A method for taking images of an object based on return light from the object irradiated with light, the method comprising:
instructing independently to change positions of a plurality of planes intersecting each other; and
controlling a scanning unit to scan the light on regions of the object corresponding to the changed positions.

28. A non-transitory tangible medium having recorded thereon a program for causing a computer to perform steps of the method according to claim 27.

29. A method according to claim 27, wherein the object is a subject's eye, and
wherein the scanning unit is located so that the light scanned by the scanning unit passes through the same position on an anterior ocular segment of the subject's eye.

* * * * *